(12) United States Patent
Mathews (10) Patent No.: US 10,086,165 B2
(45) Date of Patent: *Oct. 2, 2018

(54) AUSCULTATION INTERFACE

(71) Applicant: John F. Mathews, Athens, NY (US)

(72) Inventor: John F. Mathews, Athens, NY (US)

( * ) Notice: Subject to any disclaimer, the term of this patent is extended or adjusted under 35 U.S.C. 154(b) by 515 days.

This patent is subject to a terminal disclaimer.

(21) Appl. No.: 14/704,817

(22) Filed: May 5, 2015

(65) Prior Publication Data

US 2015/0231356 A1 Aug. 20, 2015

Related U.S. Application Data

(63) Continuation of application No. 12/145,293, filed on Jun. 24, 2008, now Pat. No. 9,050,430.

(51) Int. Cl.
| | |
|---|---|
| *A61M 16/08* | (2006.01) |
| *A61B 7/02* | (2006.01) |
| *A61B 7/00* | (2006.01) |
| *A61M 16/00* | (2006.01) |
| *A61M 16/04* | (2006.01) |

(52) U.S. Cl.
CPC ......... *A61M 16/0841* (2014.02); *A61B 7/003* (2013.01); *A61B 7/02* (2013.01); *A61M 16/0057* (2013.01); *A61M 16/04* (2013.01); *A61M 16/0833* (2014.02); *A61M 16/0883* (2014.02)

(58) Field of Classification Search
CPC .... A61J 15/00; A61J 15/0026; A61M 1/0047; A61M 1/008; A61M 11/02; A61M 15/0065; A61M 15/0086; A61M 15/009; A61M 16/04; A61M 16/0411; A61M 16/0456; A61M 16/0461; A61M 16/0463; A61M 16/0479; A61M 16/08; A61M 16/0808; A61M 16/0816; A61M 16/0833; A61M 16/0875; A61M 16/10; A61M 16/208; A61M 2039/1027; A61M 2039/1066; A61M 2039/1077; A61M 2202/0482; A61M 2205/3368; A61M 2205/7518; A61M 2209/06; A61M 2210/0618; A61M 2210/0625;
(Continued)

(56) References Cited

U.S. PATENT DOCUMENTS

| | | | | |
|---|---|---|---|---|
| 4,484,583 | A | * 11/1984 | Graham | ................. A61B 7/023 600/484 |
| 4,557,638 | A | 12/1985 | O'Neill | |

(Continued)

*Primary Examiner* — Annette Dixon
(74) *Attorney, Agent, or Firm* — GFD Patents, LLC; Gerald F. Dudding (57) ABSTRACT

The present invention provides a kit comprising a unibody auscultation interface for use with mechanical ventilation or intubation, formed from a single contiguous nonmetallic piece, the piece being shaped into a cylindrical member having opposing ends respectively adapted to frictionally connect to the external end of an endotracheal tube and either the stem of a Y piece or the patient end of a common conduit, the cylindrical member having an opening in its wall, the perimeter of which seamlessly elaborates a flared turret whose roof is adapted for non-adherent contact with the chest piece of a stethoscope; and, packaging moans for enclosing the auscultation interface aseptically. The present invention additionally provides an endotracheal tube, Y piece, breathing circuit and mechanical ventilation system incorporating the auscultation interface.

18 Claims, 5 Drawing Sheets

(58) Field of Classification Search
CPC .... A61M 2210/1053; A61M 2230/005; A61M 25/0097; A61M 39/0613; A61M 39/10; A61M 39/22; A61M 5/14; A62C 35/68; F16L 25/0045; F16L 37/008; F16L 37/12; F16L 41/12; F16L 47/30; F16L 55/24; Y10S 128/912; Y10S 604/905; A61B 5/02055; A61B 5/6853; A61B 6/4225; A61B 7/003; A61B 7/023
USPC ............ 128/200.24, 202.27, 203.12, 203.15, 128/204.23, 205.24, 207.14, 207.15, 128/207.16, 207.18, 912; 600/528, 529, 600/549, 586; 604/243, 248, 256, 268, 604/35, 533, 534, 535, 905, 97.02
See application file for complete search history.

(56) References Cited

U.S. PATENT DOCUMENTS

| | | | |
|---|---|---|---|
| 4,577,638 A * | 3/1986 | Graham | A61B 7/023 600/484 |
| 4,607,643 A | 8/1986 | Bell et al. | |
| 4,917,107 A | 4/1990 | Bell et al. | |
| 5,029,591 A * | 7/1991 | Teves | A61B 7/023 128/207.15 |
| 5,056,514 A * | 10/1991 | DuPont | A61B 7/023 128/204.23 |
| 5,191,892 A | 3/1993 | Blikken | |
| 5,295,489 A | 3/1994 | Bell et al. | |
| 5,394,880 A | 3/1995 | Atlee | |
| 5,400,797 A | 3/1995 | Ethridge | |
| 5,562,078 A | 10/1996 | Dzwonkiewicz | |
| 5,632,512 A * | 5/1997 | Guitoneau | F16L 25/0045 285/308 |
| 5,655,518 A | 8/1997 | Burden | |
| 5,853,006 A | 12/1998 | Scanlon | |
| 5,890,488 A | 4/1999 | Burden | |
| 6,119,785 A * | 9/2000 | Reise | A62C 35/68 169/16 |
| 6,443,907 B1 | 9/2002 | Mansy | |
| 6,517,497 B2 | 2/2003 | Rymut et al. | |
| 6,626,841 B1 | 9/2003 | Atlee | |
| 6,626,843 B2 | 9/2003 | Hillsman | |
| 8,882,682 B2 | 11/2014 | Qiu | |
| 9,050,430 B2 * | 6/2015 | Mathews | A61M 16/04 |
| 2005/0103346 A1 | 5/2005 | Noble | |

* cited by examiner

AUSCULTATION INTERFACE

BACKGROUND OF THE INVENTION

1.1 Field of the Invention

The invention generally pertains to the transmission and clarification of the pulmonary breath sounds of a patient breathing by means of an endotracheal tube and mechanical ventilation, and more specifically to a device for transmitting and clarifying such breath sounds to the user of a stethoscope.

1.2 Related Art

An endotracheal tube, a breathing circuit, a mechanical ventilator and ancillary equipment are used in operative procedures requiring inhalation anesthesia, or to support the breathing of patients in respiratory distress, typically in an intensive care unit or a chronic ventilator care facility. In all of these settings, the noise made by the mechanical ventilator is communicated through the endotracheal tube and the breathing circuit and interferes with the auscultation of the patient's breath sounds. Ambient noise and the presence of an elevated body mass index in a patient also interfere with the auscultation of the patient's breath sounds.

Accurate auscultation of a patient's breath sounds is important, inter alia, in:
  assuring proper placement of an endotracheal tube;
  assuring proper placement of an endotracheal tube before it is connected to the breathing circuit of a mechanical ventilator;
  detecting any displacement of the endotracheal tube after it is connected to the breathing circuit of a mechanical ventilator; and
  monitoring the patient's breathing during mechanical ventilation.

The prior art reflects both a long-felt need and a variety of imperfect approaches to meeting the long felt need for isolation and clarification of the patient's breath sounds over the noise of the ventilator, the muting occasioned by patients with a high body mass index, as well as the ambient noise introduced by the operative or intensive care environment. The large variety of approaches used to isolate and clarify a patient's breath sounds relative to extraneous noise demonstrates the persistent nature of this problem. The approaches have generally fallen into two classes.

2.1 in-Line Approach

The "in-line" approach to isolating and clarifying breath sounds during mechanical intubation calls for the attachment of a stethoscope to a nasal endotracheal tube or mechanical ventilation system by coupling means, typically inserted between the external end of an endotracheal tube and patient end of an associated breathing circuit.

U.S. Pat. No. 5,056,514, Endotracheal stethoscope, issued to DuPont on Oct. 15, 1991, is exemplary of the in-line approach, and teaches a combination of a stethoscope and an endotracheal tube, wherein the conventional chest piece of the stethoscope is removed, and the stethoscope's hose is instead connected to the side-port of a drum that forms an amplifying chamber over a membrane stretched across its base. The drum telescopically inserts into and is permanently fixed to a radially projecting cylindrical stem of a (T-shaped) tube, which tube is fitted between the external end of an oro-pharyngeal endotracheal tube and the patient end of its associated breathing circuit using opposing, collar-like, press-fit or screw-thread connectors.

The use of DuPont's invention, either as combination, or as stethoscopic device, or as an endotracheal apparatus, entails no simple apposition of the chest piece of a stethoscope to any aspect of a mechanical ventilation system. Rather, DuPont's invention requires that a stethoscope's chest piece be replaced by the aforesaid drum and that the stethoscope's hose be fitted to the aforesaid side port of the drum. DuPont's invention effectively supplants the stethoscope's chest piece with the drum's membrane, and expressly makes a stethoscope's hose continuous with and part of the mechanical ventilation system.

2.2 Off-Line Approach

The "off-line" approach to isolating and clarifying breath sounds during intubation generally calls for the detachment of the external end of a nasal endotracheal tube from its associated breathing circuit, and the attachment of a device that couples a stethoscope to the external end of a nasal endotracheal tube in a patient capable of spontaneous breathing. After the patient's breath sounds are auscultated, the stethoscopic coupling device is removed and the endotracheal tube is possibly re-connected to its associated breathing circuit set. Devices embodying the off-line approach do not appear attachable to ambu bags while in use.

U.S. Pat. Nos. 5,655,518 & 5,890,488, Coupling device for a stethoscope and an endotracheal tube, issued to Burden on Aug. 12, 1997 and Apr. 6, 1999, respectively, are exemplary of the off-line approach. These patents teach a stethoscope wherein the conventional chest piece of the stethoscope is replaced with a membrane incorporated in a multi-component T-shaped coupling tube that is disposed between the external end of a nasal endotracheal tube and its associated breathing circuit set by metal connectors. This device detachably secures the stethoscope hose to the nasal endotracheal tube for auscultation of breath sounds.

As an additional example of the off-line approach, U.S. Pat. No. 5,562,078, Endotracheal tube/stethoscope connector, issued to Dzwonkiewicz on Oct. 8, 1996, teaches a conical, hollow-bodied stethoscope connector, whose apical end fits over and connects to the external end of an endotracheal tube and whose base includes a structure for release-ably attaching the chest piece of a stethoscope. This device also detachably secures the stethoscope hose to the nasal endotracheal tube for auscultation of breath sounds.

2.3 Summary of the Problem in the Prior Art

From the foregoing examples, it is clear that the problem of clarification and isolation of a patient's breath sounds during endotracheal intubation has been approached by either:
  an in-line approach, in which a stethoscope effectively intrudes upon the mechanical ventilation system and made a part thereof; or,
  an off-line approach, in which relatively complex mechanical devices improve auscultation by coupling a stethoscope to an endotracheal tube only when the mechanical ventilator and its breathing circuit are uncoupled or excluded from an endotracheal tube or ambu bag.

However:
  the in-line approach, disadvantageously encumbers the mechanical ventilation system and delays the auscultation of breath sounds, owing to the need for mechanical interconnections or the assembly of coupling components; and
  the off-line approach disadvantageously dissembles or excludes the mechanical ventilation system and enables auscultation of breath sounds only when mechanical ventilation is withdrawn.

A first embodiment of the present invention overcomes these and other limitations by providing an aseptically pre-packaged kit containing a non-metallic auscultation interface for use during endotracheal intubation or mechanical ventilation that:

1) is leak-proof and seamless, being of unibody construction, and thus without moving parts;
2) provides non-fixed and non-adherent connectivity with the chest piece of a stethoscope, with no requirement for removal of the chest piece from the hose of a stethoscope;
3) provides frictional telescopic connectivity with both the endotracheal tube and its associated breathing circuit, thereby eliminating the need for connectors; and
4) provides recyclability or disposability.

Embodiments 2 through 7 of the present invention overcome the limitations of the prior art and provide the same advantages of the first embodiment by providing a non-metallic auscultation interface for use during endotracheal intubation or mechanical ventilation that augments and is seamlessly, continuously and permanently integrated with either:

1) the external end of an endotracheal tube; or
2) the stem of a Y piece; or,
3) either the inspiratory arm or the expiratory arm of the Y piece; or,
4) either the inspiratory limb or the expiratory limb of the breathing circuit, preferably at a location proximal to the Y piece.

The present invention combines the advantages of both the off-line and in-line approaches without their respective disadvantages because the invention alone becomes part of the mechanical ventilation system, without incorporating a stethoscope; and, the mechanical ventilation system need not be dissembled or excluded in order to obtain isolated and clear breath sounds.

The present invention provides these advantages by providing either: a detachable or a permanent in-line interface to which the chest piece of a stethoscope may be apposed, rather than being attached or connected. The present invention is an expression of elegance, simplicity and economy in keeping with the needs of 21st century medicine.

SUMMARY OF THE INVENTION

In a first embodiment, the present invention provides a kit comprising (a) a leak-proof, seamless unibody auscultation interface for use with mechanical ventilation or intubation, formed from a single contiguous non-metallic piece, the piece being shaped into a cylindrical member having opposing ends respectively adapted to frictionally connect to the external end of an endotracheal tube and either the stem of a "Y" piece or the patient end of a common conduit, the cylindrical member having an opening in its wall the perimeter of which seamlessly elaborates a flared turret whose roof is adapted for non-adherent contact with the chest piece of a stethoscope; and, (b) packaging means for enclosing the auscultation interface aseptically, wherein the auscultation interface is removeably secured relative to the packaging means to allow access for use with mechanical ventilation.

In a second embodiment, the present invention provides an endotracheal tube whose external end continuously and seamlessly expands into an open-ended chamber having the shape and function of the auscultation interface of the first embodiment of the present invention; i.e., the second embodiment provides a leak-proof, seamless unibody endotracheal tube whose external end terminates in an auscultation interface for use with mechanical ventilation or intubation, formed as a seamless continuation of the endotracheal tube, the auscultation interface being shaped into a cylindrical member having an open-end adapted to frictionally connect to the stem of a Y piece or the patient end of the optional common conduit of a breathing circuit, the cylindrical member further having an opening in its wall the perimeter of which seamlessly elaborates a flared turret whose roof is adapted for non-adherent contact with the chest piece of a stethoscope.

In a third embodiment, the present invention provides a Y piece whose stem continuously and seamlessly expands into an open-ended chamber having the shape and function of the auscultation interface of the first embodiment of the present invention; i.e., the third embodiment provides a leak-proof, seamless unibody Y piece whose stem terminates in an auscultation interface for use with mechanical ventilation, formed as a seamless continuation of the Y piece, the auscultation interface being shaped into a cylindrical member having an open-end adapted to frictionally connect to the external end of an endotracheal tube, the cylindrical member further having an opening in its wall the perimeter of which seamlessly elaborates a flared turret whose roof is adapted for non-adherent contact with the chest piece of a stethoscope.

In a fourth embodiment, the present invention provides a Y piece whose inspiratory arm continuously and seamlessly expands into an open-ended chamber having the shape and function of the auscultation interface of the first embodiment of the present invention i.e., the fourth embodiment provides a leak-proof, seamless unibody Y piece whose inspiratory arm terminates in an auscultation interface for use with mechanical ventilation, formed as a seamless continuation of the Y piece, the auscultation interface being shaped into a cylindrical member having an open-end adapted to frictionally connect to the end of an inspiratory limb of a breathing circuit, the cylindrical member further having an opening in its wall the perimeter of which seamlessly elaborates a flared turret whose roof is adapted for non-adherent contact with the chest piece of a stethoscope.

In a fifth embodiment, the present invention provides a Y piece whose expiratory arm continuously and seamlessly expands into an open-ended chamber having the shape and function of the auscultation interface of the first embodiment of the present invention; i.e., the fifth embodiment provides a leak-proof, seamless unibody Y piece whose expiratory arm terminates in an auscultation interface for use with mechanical ventilation, formed as a seamless continuation of the Y piece, the auscultation interface being shaped into a cylindrical member having an open-end adapted to frictionally connect to the end of an expiratory limb of a breathing circuit, the cylindrical member further having an opening in its wall the perimeter of which seamlessly elaborates a flared turret whose roof is adapted for non-adherent contact with the chest piece of a stethoscope.

In a sixth embodiment, the present invention provides a breathing circuit, a portion of whose inspiratory limb continuously and seamlessly expands into an bubble having the shape and function of the auscultation interface of the first embodiment of the present invention; i.e., the sixth embodiment provides a leak-proof, seamless unibody breathing circuit whose inspiratory limb contains an auscultation interface for use with mechanical ventilation, formed as a seamless continuation of the inspiratory limb, the auscultation interface being shaped into a cylindrical member, the cylindrical member further having an opening in its wall the perimeter of which seamlessly elaborates a flared turret whose roof is adapted for non-adherent contact with the chest piece of a stethoscope.

In a seventh embodiment, the present invention provides a breathing circuit, a portion of whose expiratory limb continuously and seamlessly expands into an bubble having the shape and function of the auscultation interface of the first embodiment of the present invention; i.e., the seventh embodiment provides a leak-proof, seamless unibody breathing circuit whose expiratory limb contains an auscultation interface for use with mechanical ventilation, formed as a continuation of the expiratory limb, the auscultation interface being shaped into a cylindrical member, the cylindrical member further having an opening in its wall the perimeter of which seamlessly elaborates a flared turret whose roof is adapted for non-adherent contact with the chest piece of a stethoscope.

DETAILED DESCRIPTION OF THE INVENTION

Before the present invention is described, it is to be understood that this invention is not limited to the particular embodiments described, as these may, of course, vary. It is also to be understood that the terminology used herein is for the purpose of describing only the particular embodiments, and is not intended to be limiting, because the scope of the present invention will be limited only by the appended claims.

Mechanical Ventilation

A mechanical ventilation system may be used to deliver air enriched with oxygen to a patient with respiratory distress, or it may be used to deliver air enriched with oxygen together with inhalation anesthetics to a patient undergoing surgery. Typically, a mechanical ventilation system includes controls for assisting or controlling breathing, exhaled volume indicators, alarm systems, positive end expiratory pressure ("PEEP") valves, pressure indicators, gas concentration monitors, flow indicators, heated humidifiers for warming and humidifying the breathing gas and tubing for interconnecting these components with each other and the patient.

Often the anesthesiologist, who monitors and controls the system, must add ancillary devices and accessories to the system, as determined by factors such as the physiological status of the patient, the nature of the surgical procedure, the anesthetic technique employed, etc. For the foregoing reasons, the use of a stethoscope for auscultation of the patient's breath sounds is included among the anesthesiologist's monitoring duties.

Figure 1:
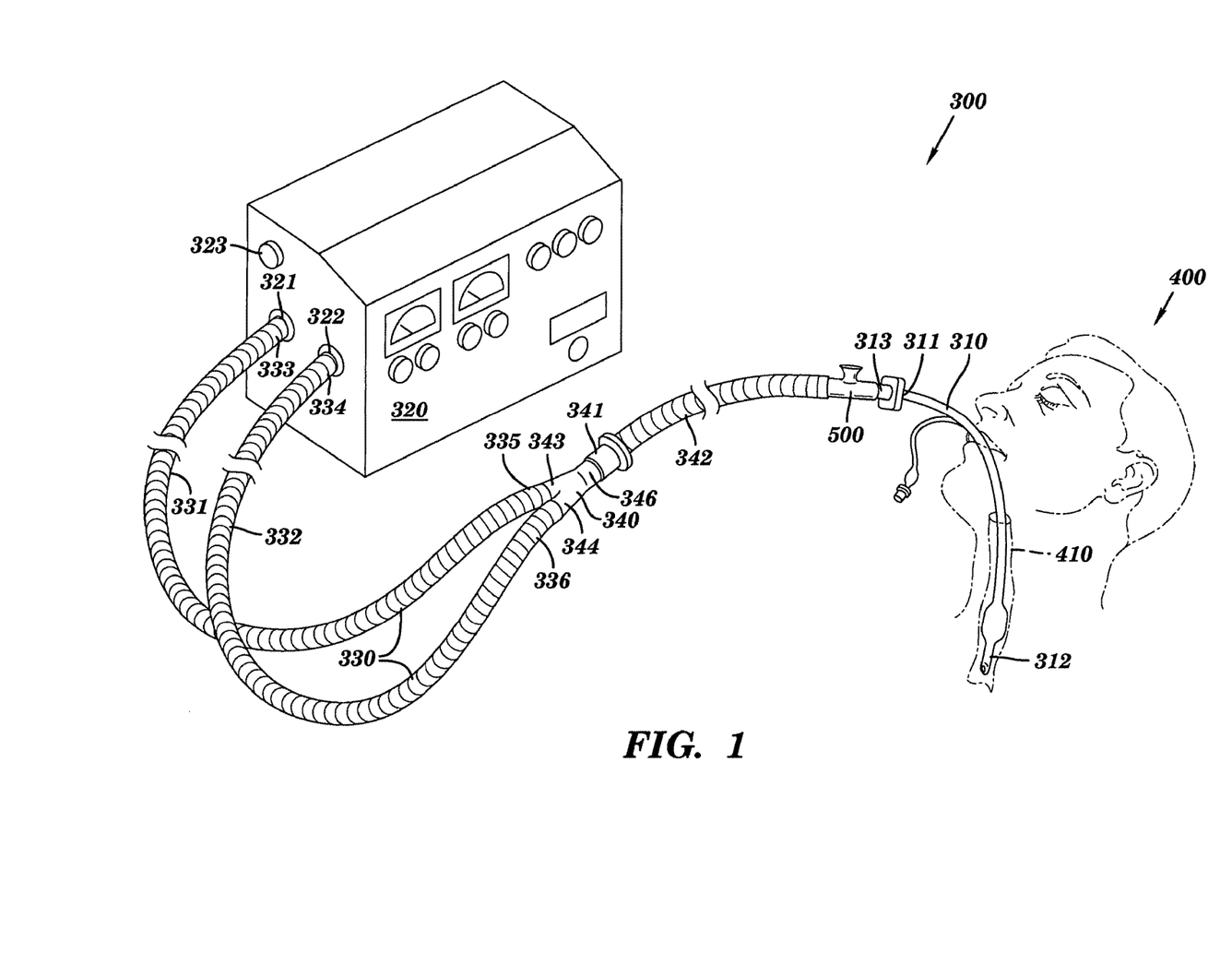
FIG. 1 shows the auscultation interface frictionally attached between the patient end of a common conduit connected to the stem of a Y piece and the external end of an endotracheal tube.
Figure 2:
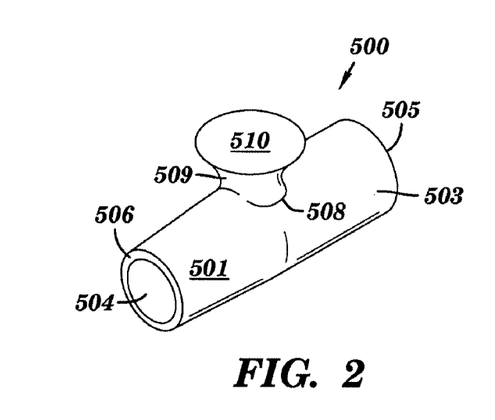
FIG. 2 shows a perspective view of the auscultation interface.

FIG. 1 illustrates a mechanical ventilation system 300 supporting a patient 400. Mechanical ventilation system 300 generally comprises:

a) an endotracheal tube 310 for insertion into the airway 410 of patient 400;

b) a mechanical ventilator 320; and c) a breathing circuit 330, that forms a closed or semi-closed gaseous circuit between mechanical ventilator 320 and endotracheal tube 310.

Mechanical ventilator 320 generally includes an inspiration port 321, an expiration port 322 and an exhaust port 323.

Breathing circuit 330 is typically composed of a flexible corrugated plastic tube comprising an inspiratory limb 331 and an expiratory limb 332. The distal end 333 of inspiratory limb 331 connects to mechanical ventilator 320 via inspiration port 321; and, the distal end 334 of expiratory limb 332 connects to mechanical ventilator 320 via expiratory port 322. The proximal end 335 of inspiratory limb 331 and the proximal end 336 of expiratory limb 332 connect to a common "Y" piece 340 to form common conduit 342 by means of connector 341 to "Y" piece stem 346.

"Y" piece 340 is a hollow plastic joint at which inspiratory limb 331 and expiratory limb 332 converge to form a "Y" piece stem 346 by means of respective connections to an inspiratory arm 343 of "Y" piece 340, and an expiratory arm 344 of "Y" piece 340. "Y" piece stem 346 may optionally be extended into a common conduit 342 by means of a frictional connector 341. In FIG. 1, breathing circuit 330 has effectively been joined to the external end 311 of endotracheal tube 310, whose internal end 312 has been inserted into the oro-pharyngeal or nasopharyngeal pathway of patient 400. External end 311 of endotracheal tube 310 is typically provided with a connector 313 for attachment to the patient-end of optional common conduit 342, or, more typically, directly to "Y" piece stem 346.

The Invention.

In FIG. 1, auscultation interface 500 is shown in an exemplary disposition as frictionally attached to the patient-end of optional common conduit 342 and connector 313 at the external end 311 of endotracheal tube 310. To obtain dear breath sounds, an anesthesiologist or other patient-care provider, simply places the chest piece of a stethoscope against the elevated portion of auscultation interface 500, more fully described below.

Mechanical ventilation system 300 may also include the various ancillary devices and accessories referred to above. However, these are not essential to the presentation of the instant invention and are accordingly omitted to avoid obscuring details of the invention.

Figure 3:
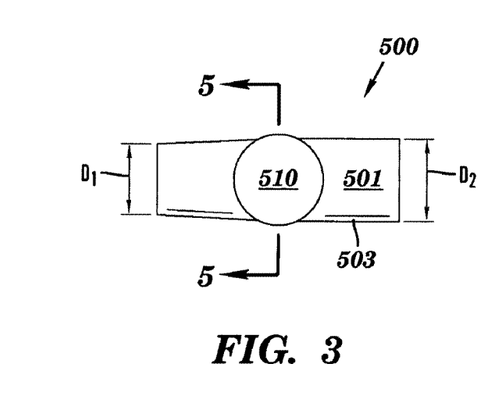
FIG. 3 shows a top view of the auscultation interface.
Figure 4:
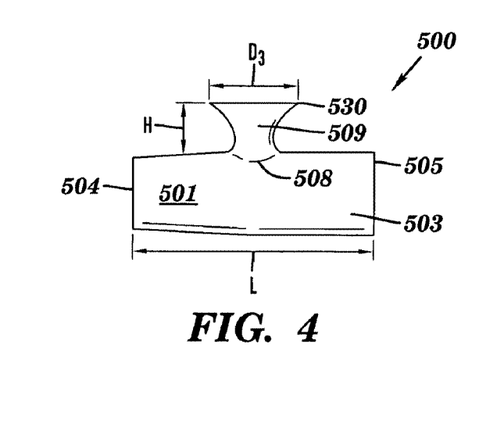
FIG. 4 shows a side view of the auscultation interface.
Figure 5:
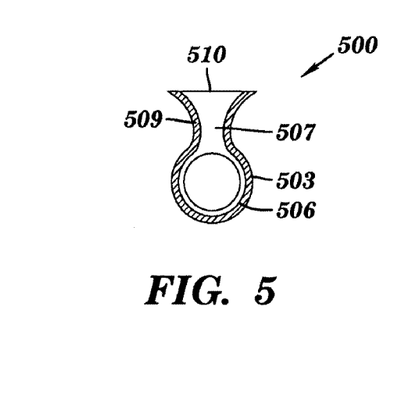
FIG. 5 shows an axial cross-sectional view of the auscultation interface taken through line 5-5 of FIG. 3.

Referring now to FIGS. 2 through 5, auscultation interface 500 of the present invention is shown in greater detail. As shown in FIGS. 2 through 5, auscultation interface 500 is comprised of a single, seamless, leak-proof, and contiguous (i.e., "unibody") hollow non-metallic piece 501. Unibody piece 501 is shaped into a generally cylindrical member 503 having a length L (FIG. 4). L is preferably 45 mm but may be longer or shorter.

Cylindrical member 503 has a first open end 504 having an inner diameter of D1 (FIG. 3) and an opposing second open end 505 having an inner diameter of D2 (FIG. 3). First open end 504 is adapted to frictionally connect to the external end 311 of endotracheal tube 310 (optionally using connector 313); and, second open end 505 is adapted to frictionally connect to the patient end of optional common conduit 342 or "Y" piece stem 346 (optionally using another connector, such as 341 in FIG. 1). As the standard inner diameter for an endotracheal tube is 15 mm and the standard inner diameter of the patient end of "Y" piece stem 346 is 22 mm, D1 is preferably just sufficiently larger or smaller than 15 mm to enable a snug frictional fit to the external end of a standard endotracheal tube or connector 313; and, D2 is preferably just sufficiently larger or smaller than 21 mm to enable a snug frictional fit to "Y" piece stem 346 or patient end of optional common conduit 342.

The wall 506 (FIG. 2 & FIG. 5) of cylindrical member 503 (FIGS. 2, 3, 4) is provided with an opening 507 (FIG. 5), whose perimeter 508 (FIG. 2 & FIG. 4) seamlessly elaborates a hollow flared turret 509 (FIGS. 2, 4, 5), resembling the horn of a trumpet in shape, having a contiguous generally curvilinear, but preferably circular roof 510 adapted for non-adherent contact with the chest piece of a stethoscope (not shown in figures). Hollow flared turret 509 has a variable height H (FIG. 4). Height H is preferably at least 2 mm. Roof 510 preferably has a diameter D3 of 28 mm, that runs between opposing points 530 (FIG. 4). D3 may range between the average outer diameter of the bell of a chest piece of a pediatric stethoscope and the average outer diameter of the diaphragm of an adult stethoscope. Roof 510 is preferably flat but may be vaulted or domed. The thickness of roof 510 may be attenuated so that it is less than the thickness of wall 506.

The wall 506 of cylindrical member 503 may have a thickness of about 2 mm, depending on manufacturing mold constraints, which thickness is maintained in the walls and flared turret 509, but not necessarily in roof 510. As indicated, roof 510 may be thinner than flared turret 509 and wall 506. Unibody hollow non-metallic piece 501 may be made of plastics, such as, for example, acrylonitrile butadiene styrene (ABS), polyamide, polypropylene, polyethylene (PE), polyethylene terephthalate (PET), polymethylmethacrylate (PMMA), polytetrafluoroethylene (PTFE) or nylon.

Figure 6:
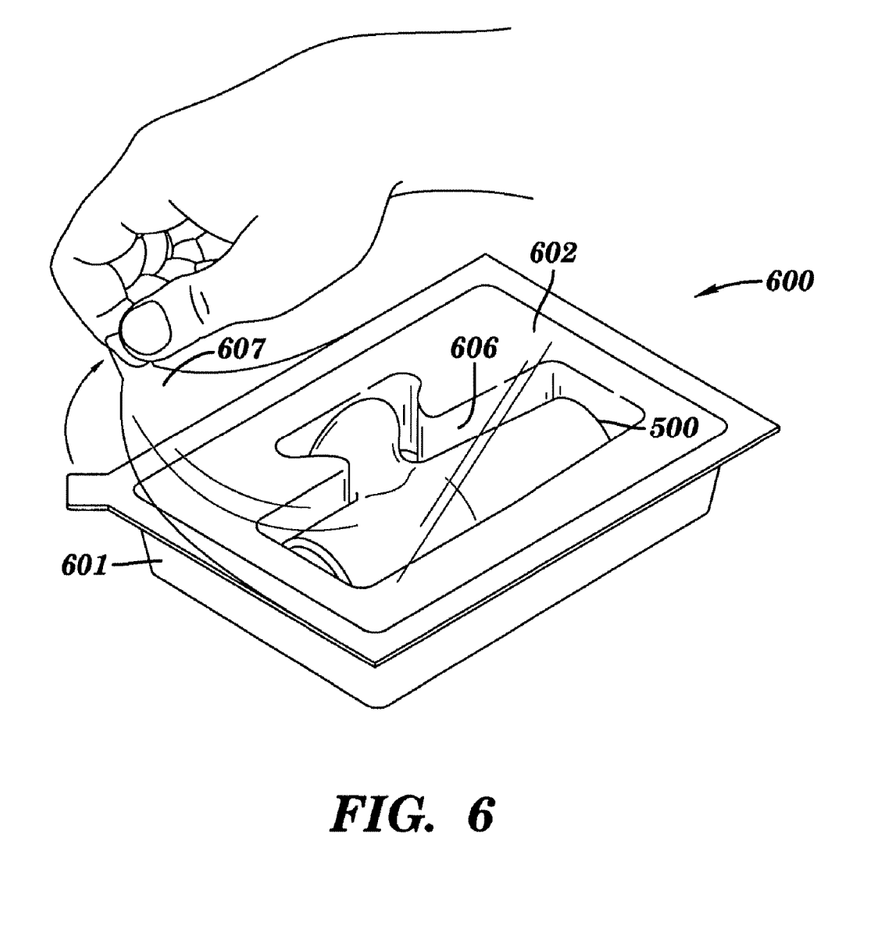
FIG. 6 shows a perspective view of a kit containing the auscultation interface, which is about to be deployed from its containment means.\

FIG. 6 shows auscultation interface 500 provided in a kit 600. Kit 600 comprises a box 601 supporting a platform 602 whose surface has a well 606 whose contour and depth allow it to detachably receive and support auscultation interface 500. The depth of well 606 is such that no aspect of auscultation interface 500 rises above the level of the surface of platform 602 when it is placed therein. Box 601 and platform 602 are preferably formed of plastic. Well 606 is covered with a top-sealing sheet 607 whose margins are adherently secured to supporting platform 602. Top-sealing sheet 607 is preferably made from a strong, but pliable transparent material, such as, for example Mylar®. Top-sealing sheet 607 would typically have visual indicia printed on it, such as descriptions of how to use the auscultation interface.

In practice kit 600 is delivered to an operating room or intensive care unit. Top-sealing sheet 607 is removed and auscultation interface 500 is removed from well 606 for use.

Following endotracheal intubation, first open end 504 of auscultation interface 500 is frictionally connected to the external end 311 of the endotracheal tube 310. An anesthesiologist or other health care provider may then apply the chest piece of a stethoscope to roof 510 of auscultation interface 500 to receive clear auscultation of the patient's breath sounds. Second open end 505 of auscultation interface 500 may either be left open or concurrently frictionally connected to an ambu bag. Following initial auscultation of the patient's breath sounds second open end 505 of auscultation interface 500 is frictionally connected to the "Y" piece stem 346 or the patient end of optional common conduit 342. Thereafter, auscultation interface 500 is available for auscultation of the patient's breath sounds throughout the course of mechanical ventilation until extubation.

As a freestanding device, provided in kit form, auscultation interface 500 may be interconnected anywhere along the breathing circuit of a mechanical ventilation system.

For example, the auscultation interface may have opposing ends respectively adapted to frictionally connect to opposing sectioned ends of an inspiratory limb of the breathing circuit; or, the auscultation interface may have opposing ends respectively adapted to frictionally connect to opposing sectioned ends of the expiratory limb of the breathing circuit.

As another example, the auscultation interface may have opposing ends respectively adapted to frictionally connect to an inspiratory arm of the Y piece and an inspiratory limb of the breathing circuit; or, the auscultation interface may have opposing ends respectively adapted to frictionally connect to an expiratory arm of the Y piece and an expiratory limb of the breathing circuit.

Alternatively, device 500 may be placed directly between Y-piece stem 346 and connector 313.

Figure 7:
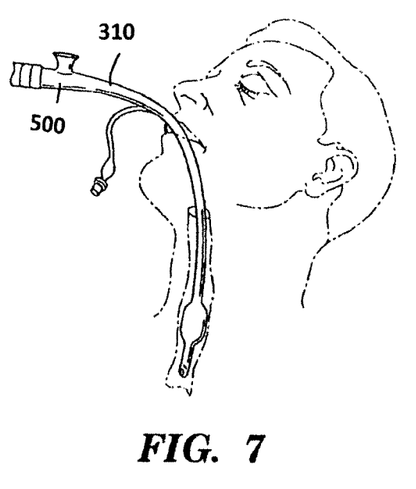
FIG. 7 shows the auscultation interface seamlessly, continuously and permanently integrated with the external end of an endotracheal tube.
Figure 8A:
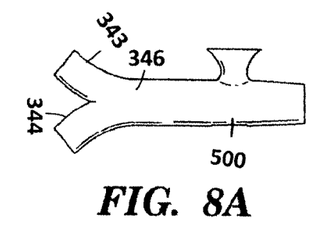
FIG. 8A shows the auscultation interface seamlessly, continuously and permanently integrated with the stem of a Y piece.
Figure 8B:
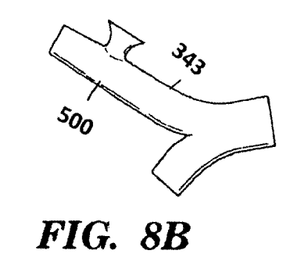
FIG. 8B shows the auscultation interface seamlessly, continuously and permanently integrated with an inspiratory arm of a Y piece.
Figure 8C:
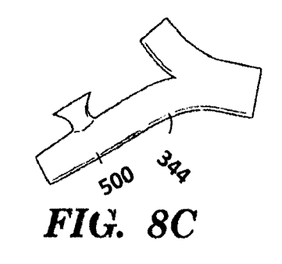
FIG. 8C shows the auscultation interface seamlessly, continuously and permanently integrated with an expiratory arm of a Y piece.
Figure 9A:
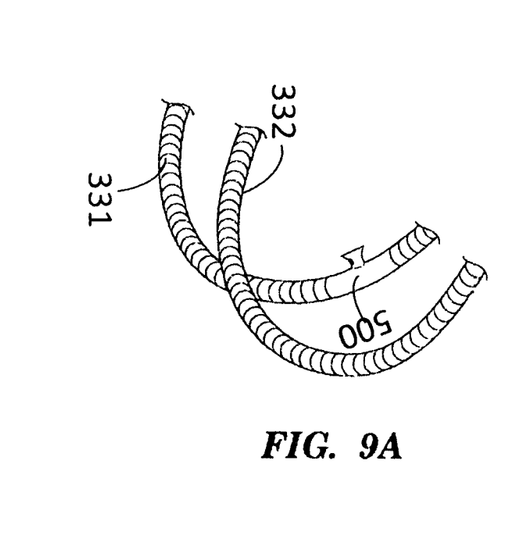
FIG. 9A shows the auscultation interface seamlessly, continuously and permanently integrated with an inspiratory limb of a breathing circuit.
Figure 9B:
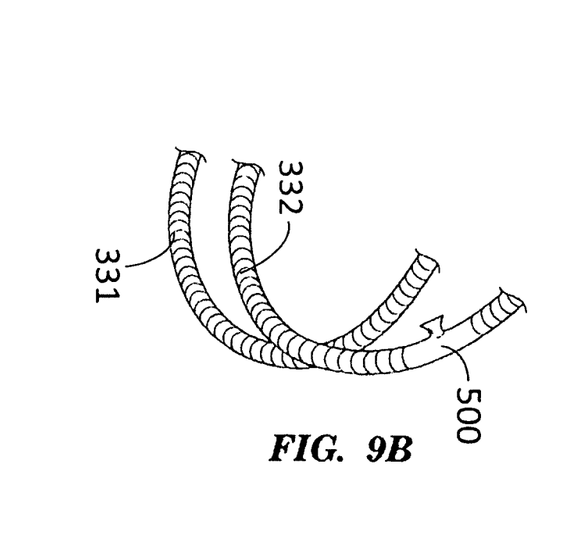
FIG. 9B shows the auscultation interface seamlessly, continuously and permanently integrated with an expiratory limb of a breathing circuit.

FIGS. 7, 8, 9 show alternative embodiments of the invention wherein auscultation interface 500 is not provided as a free-standing device in kit form, rather, it is provided as an integral aspect of an endotracheal tube or as an integral aspect of a component of a mechanical ventilation.

FIG. 7 shows auscultation interface 500 as an integral part of an endotracheal tube 310, as shown in FIG. 1, in the form of a continuous seamless expansion of the endotracheal tube's external end 311 having the above-described shape and function of auscultation interface 500.

In a second embodiment, the present invention provides an endotracheal tube whose external end continuously and seamlessly expands into an open-ended chamber having the shape and function of the auscultation interface of the first embodiment of the present invention; i.e., the second embodiment provides a leak-proof, seamless unibody endotracheal tube whose external end terminates in an auscultation interface for use with mechanical ventilation or intubation, formed as a seamless continuation of the endotracheal tube, the auscultation interface being shaped into a cylindrical member having an open-end adapted to frictionally connect to the "Y" piece stem or patient end of the optional common conduit of a breathing circuit, the cylindrical member further having an opening in its wall, the perimeter of which seamlessly elaborates a flared turret whose roof is adapted for non-adherent contact with the chest piece of a stethoscope.

FIG. 8A shows auscultation interface 500 as an integral part of the stem 346, as shown in FIG. 1, of a Y piece in the form of a continuous seamless expansion of the Y piece stem 346, having the above-described shape and function of auscultation interface 500.

In a third embodiment, the present invention provides a Y piece whose stem continuously and seamlessly expands into an open-ended chamber having the shape and function of the auscultation interface of the first embodiment of the present invention; i.e., the third embodiment provides a leak-proof, seamless unibody Y piece whose stem terminates in an auscultation interface for use with mechanical ventilation or intubation, formed as a seamless continuation of the Y piece, the auscultation interface being shaped into a cylindrical member having an open-end adapted to frictionally connect to the external end of an endotracheal tube, the cylindrical member further having an opening in its wall, the perimeter of which seamlessly elaborates a flared turret whose roof is adapted for non-adherent contact with the chest piece of a stethoscope.

FIG. 8B shows auscultation interface 500 as an integral part of an inspiratory arm 343, as shown in FIG. 1, of a Y piece in the form of a continuous seamless expansion of the inspiratory arm 343 in the above-described shape of auscultation interface 500.

In a fourth embodiment, the present invention provides a Y piece whose inspiratory arm continuously and seamlessly expands into an open-ended chamber having the shape and function of the auscultation interface of the first embodiment of the present invention i.e., the fourth embodiment provides a leak-proof, seamless unibody Y piece whose inspiratory arm terminates in an auscultation interface for use with mechanical ventilation or intubation, formed as a seamless continuation of the Y piece, the auscultation interface being shaped into a cylindrical member having an open-end adapted to frictionally connect to the end of an inspiratory limb of a breathing circuit, the cylindrical member further having an opening in its wall, the perimeter of which seamlessly elaborates a flared turret whose roof is adapted for non-adherent contact with the chest piece of a stethoscope.

FIG. 8C shows auscultation interface 500 as an integral part of an expiratory arm 344, as shown in FIG. 1, of a Y piece in the form of a continuous seamless expansion of the expiratory arm 344 in the above-described shape of auscultation interface 500.

In a fifth embodiment, the present invention provides a Y piece whose expiratory arm continuously and seamlessly expands into an open-ended chamber having the shape and function of the auscultation interface of the first embodiment of the present invention; i.e., the fifth embodiment provides a leak-proof, seamless unibody Y piece whose expiratory arm terminates in an auscultation interface for use with mechanical ventilation or intubation, formed as a seamless continuation of the Y piece, the auscultation interface being shaped into a cylindrical member having an open-end adapted to frictionally connect to the end of an expiratory limb of a breathing circuit, the cylindrical member further having an opening in its wall the perimeter of which seamlessly elaborates a flared turret whose roof is adapted for non-adherent contact with the chest piece of a stethoscope.

FIG. 9A shows auscultation interface 500 as an integral part of a representative inspiratory limb 331, as shown in FIG. 1, of a breathing circuit in the form of a continuous seamless expansive chamber, arising from the inspiratory limb, having the above-described shape and function of auscultation interface 500.

In a sixth embodiment, the present invention provides a breathing circuit, a portion of whose inspiratory limb continuously and seamlessly expands into an chamber having the shape and function of the auscultation interface of the first embodiment of the present invention; i.e., the sixth embodiment provides a leak-proof, seamless unibody breathing circuit whose inspiratory limb contains an auscultation interface for use with mechanical ventilation or intubation, formed as a seamless continuation of the inspiratory limb, the auscultation interface being shaped into a cylindrical member, the cylindrical member further having an opening in its wall, the perimeter of which seamlessly elaborates a flared turret whose roof is adapted for non-adherent contact with the chest piece of a stethoscope.

FIG. 9B shows auscultation interface 500 as an integral part of a representative expiratory limb 332, as shown in FIG. 1, of a breathing circuit in the form of a continuous seamless expansive chamber, arising from the expiratory limb, having the above-described shape of auscultation interface 500.

In a seventh embodiment, the present invention provides a breathing circuit, a portion of whose expiratory limb continuously and seamlessly expands into a chamber having the shape and function of the auscultation interface of the first embodiment of the present invention; i.e., the seventh embodiment provides a leak-proof, seamless unibody breathing circuit whose expiratory limb contains an auscultation interface for use with mechanical ventilation or intubation, formed as a continuation of the expiratory limb, the auscultation interface being shaped into a cylindrical member, the cylindrical member further having an opening in its wall, the perimeter of which seamlessly elaborates a flared turret whose roof is adapted for non-adherent contact with the chest piece of a stethoscope.

While the invention has been disclosed in connection with the embodiments depicted herein, it will be apparent to one of ordinary skill in the art that various modifications and substitutions may be made to these embodiments without departing in any way from the scope of the invention as defined in the following claims.

I claim:

1. A leak-proof auscultation interface either detachably or permanently in-line with a breathing circuit, for use with mechanical ventilation and configured to be used with a stethoscope having a chest piece, comprising: a cylindrical member having opposing ends, wherein the opposing ends are either detachably or permanently in-line with the breathing circuit, the cylindrical member further having an opening in its wall, the perimeter of which of the wall seamlessly elaborating a flared turret, and wherein the roof of the turret is adapted for non-adherent contact with the chest piece of a stethoscope.

2. The auscultation interface of claim 1, wherein a diameter of the roof of the auscultation interface ranges between the average outer diameter of a diaphragm of a chest piece of a pediatric stethoscope and the average outer diameter of a diaphragm of an adult stethoscope.

3. The auscultation interface of claim 1, wherein the roof of the auscultation interface is flat.

4. The auscultation interface of claim 1, wherein the roof of the auscultation interface is vaulted.

5. The auscultation interface of claim 1, wherein the cylindrical member is made from a material selected from the group consisting of acrylonitrile butadiene styrene (ABS), polyimide, polypropylene, polyethylene (PE), polyethylene terephthalate (PET), polymethylmethacrylate (PMMA), polytetrafluoroethylene (PTFE), and nylon.

6. The auscultation interface of claim 1, wherein the auscultation interface is disposable.

7. The auscultation interface of claim 1, wherein opposing ends of the auscultation interface are respectively adapted to frictionally connect to opposing sectioned ends of the breathing circuit.

8. The auscultation interface of claim 1, wherein the auscultation interface is a continuous, seamless expansive chamber of the breathing circuit.

9. The auscultation interface of claim 1, wherein a thickness of the roof of the auscultation interface is attenuated so that it is less than or equal to a thickness of the wall between the opposing ends.

10. A method for auscultation of a patient's breath sounds during mechanical ventilation, and configured to be used with a stethoscope having a chest piece, comprising:
providing a leak-proof auscultation interface, comprising:
a cylindrical member having opposing ends,
wherein the opposing ends are either detachably or permanently in-line with the breathing circuit, the cylindrical member further having an opening in its wall, the perimeter of the wall seamlessly elaborating a flared turret, wherein a roof of the turret is adapted for non-adherent contact with the chest piece of a stethoscope, and wherein the roof of the turret is adapted for non-adherent contact with the chest piece of a stethoscope; and
auscultation of a patient's breath sounds during mechanical ventilation by non-adherently contacting the roof of the turret with the chest piece of the stethoscope.

11. The method of claim 10, wherein a diameter of the roof ranges between the average outer diameter of a diaphragm of a chest piece of a pediatric stethoscope and the average outer diameter of a diaphragm of an adult stethoscope.

12. The method of claim 10, wherein the roof of the auscultation interface is flat.

13. The method of claim 10, wherein the roof of the auscultation interface is vaulted.

14. The method of claim 10, wherein the cylindrical member is made from a material selected from the group consisting of acrylonitrile butadiene styrene (ABS), polyimide, polypropylene, polyethylene (PE), polyethylene terephthalate (PET), polymethylmethacrylate (PMMA), polytetrafluoroethylene (PTFE), and nylon.

15. The method of claim 10, wherein the auscultation interface is disposable.

16. The method of claim 10, wherein opposing ends of the auscultation interface are respectively adapted to frictionally connect to opposing sectioned ends of the breathing circuit.

17. The method of claim 10, wherein the auscultation interface is a continuous, seamless expansive chamber of the breathing circuit.

18. The method of claim 10, wherein a thickness of the roof of the auscultation interface is attenuated so that it is less than or equal to a thickness of the wall between the opposing ends.

* * * * *